United States Patent
Andersson et al.

(10) Patent No.: US 10,578,613 B2
(45) Date of Patent: Mar. 3, 2020

(54) SOLID SUPPORT FOR IMPROVED DETECTION OF INTERACTION BETWEEN SPECIES

(71) Applicant: RIDGEVIEW INSTRUMENTS AB, Vange (SE)

(72) Inventors: Karl Andersson, Vange (SE); John Strandgard, Bjorklinge (SE)

(73) Assignee: RIDGEVIEW INSTRUMENTS AB, Vange (SE)

( * ) Notice: Subject to any disclaimer, the term of this patent is extended or adjusted under 35 U.S.C. 154(b) by 17 days.

(21) Appl. No.: 15/507,542

(22) PCT Filed: Aug. 31, 2015

(86) PCT No.: PCT/SE2015/050914
§ 371 (c)(1),
(2) Date: Feb. 28, 2017

(87) PCT Pub. No.: WO2016/036301
PCT Pub. Date: Mar. 10, 2016

(65) Prior Publication Data
US 2017/0299582 A1 Oct. 19, 2017

(30) Foreign Application Priority Data
Sep. 1, 2014 (SE) .................... 1451012-7

(51) Int. Cl.
| | | |
|---|---|---|
| G01N 33/543 | (2006.01) | |
| B01L 3/00 | (2006.01) | |
| C12M 1/00 | (2006.01) | |
| C12M 1/22 | (2006.01) | |

(52) U.S. Cl.
CPC ........ *G01N 33/54306* (2013.01); *B01L 3/502* (2013.01); *B01L 3/5085* (2013.01); *G01N 33/54366* (2013.01); *G01N 33/54373* (2013.01); *B01L 2200/025* (2013.01); *B01L 2300/0618* (2013.01); *B01L 2300/0803* (2013.01); *B01L 2300/087* (2013.01); *B01L 2300/0809* (2013.01); *B01L 2300/0832* (2013.01); *B01L 2300/0851* (2013.01); *B01L 2300/0858* (2013.01); *B01L 2300/0864* (2013.01); *B01L 2300/165* (2013.01); *B01L 2400/0457* (2013.01); *B01L 2400/086* (2013.01); *C12M 23/10* (2013.01); *C12M 23/34* (2013.01)

(58) Field of Classification Search
None
See application file for complete search history.

(56) References Cited

U.S. PATENT DOCUMENTS

| | | | |
|---|---|---|---|
| 4,294,931 A | | 10/1981 | Levin et al. |
| 5,320,808 A | * | 6/1994 | Holen ............... B01L 3/508 422/64 |
| 7,618,829 B2 | | 11/2009 | Keizer et al. |
| 7,867,753 B2 | * | 1/2011 | Andersson ......... B01L 3/508 435/287.1 |
| 8,877,141 B2 | * | 11/2014 | Yu ..................... B01L 3/5025 422/407 |
| 9,523,701 B2 | * | 12/2016 | Bunce ............. G01N 33/54366 |
| 2002/0015947 A1 | * | 2/2002 | Charlton .......... G01N 33/56983 435/5 |
| 2004/0137607 A1 | * | 7/2004 | Tanaami .......... B01L 3/502715 435/287.2 |
| 2005/0264805 A1 | * | 12/2005 | Cromwell .......... G01N 21/253 356/246 |
| 2007/0065811 A1 | * | 3/2007 | Keizer .............. B01L 3/50255 435/5 |
| 2007/0207450 A1 | * | 9/2007 | Rodgers ........... B01J 19/0046 435/3 |
| 2012/0183977 A1 | * | 7/2012 | Bunce ............. G01N 33/54366 435/7.92 |
| 2013/0122580 A1 | * | 5/2013 | Tsukada ............. C12M 23/12 435/289.1 |

FOREIGN PATENT DOCUMENTS

| | | |
|---|---|---|
| CN | 1845778 | 10/2006 |
| CN | 1922483 | 2/2007 |
| EP | 1 852 186 | 11/2007 |
| EP | 1 723 411 | 8/2013 |

OTHER PUBLICATIONS

European Office Action for Application No. 15 838 931.2, dated Jan. 17, 2019.

* cited by examiner

*Primary Examiner* — Ann Y Lam
(74) *Attorney, Agent, or Firm* — Young & Thompson

(57) ABSTRACT

Disclosed is a solid support suitable for improving the detection of how different species interact with each other. The solid support has multiple defined areas divided by low dividers, and optionally independent containers divided by high dividers, each container having at least two defined areas. The solid support is typically used in measurements where the total amount of liquid is temporarily reduced during measurement. The solid support extends the possibilities of the measurement system.

9 Claims, 15 Drawing Sheets

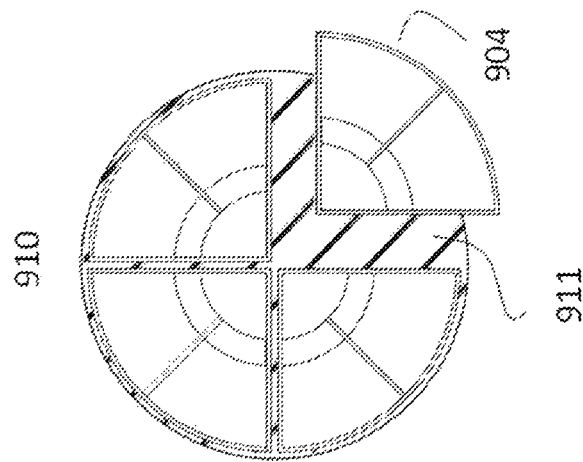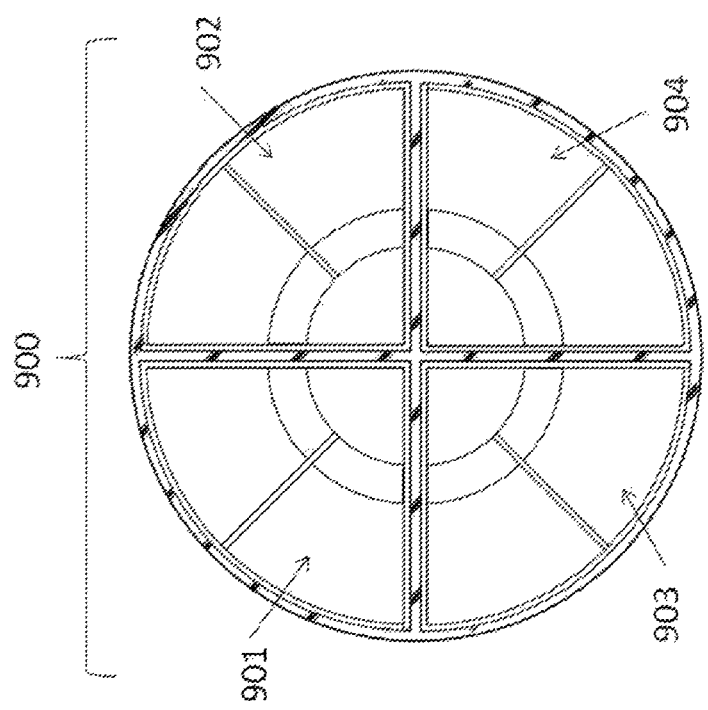
Fig. 9

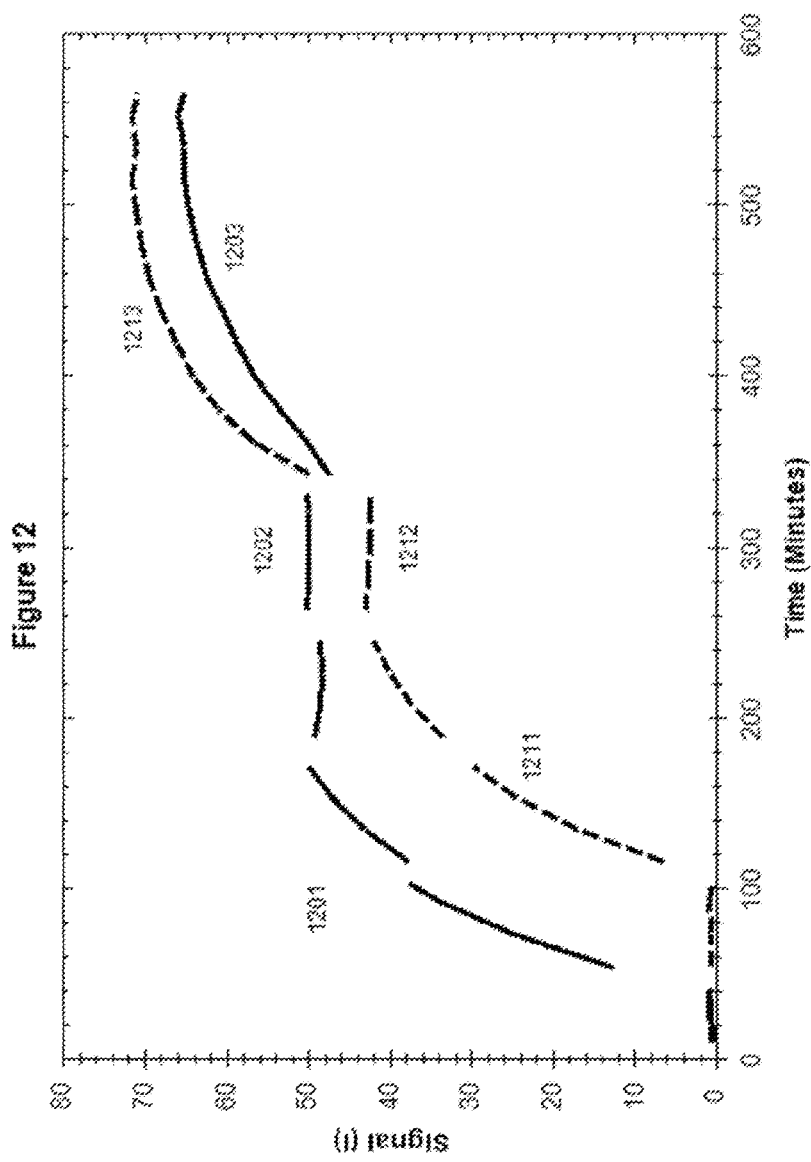

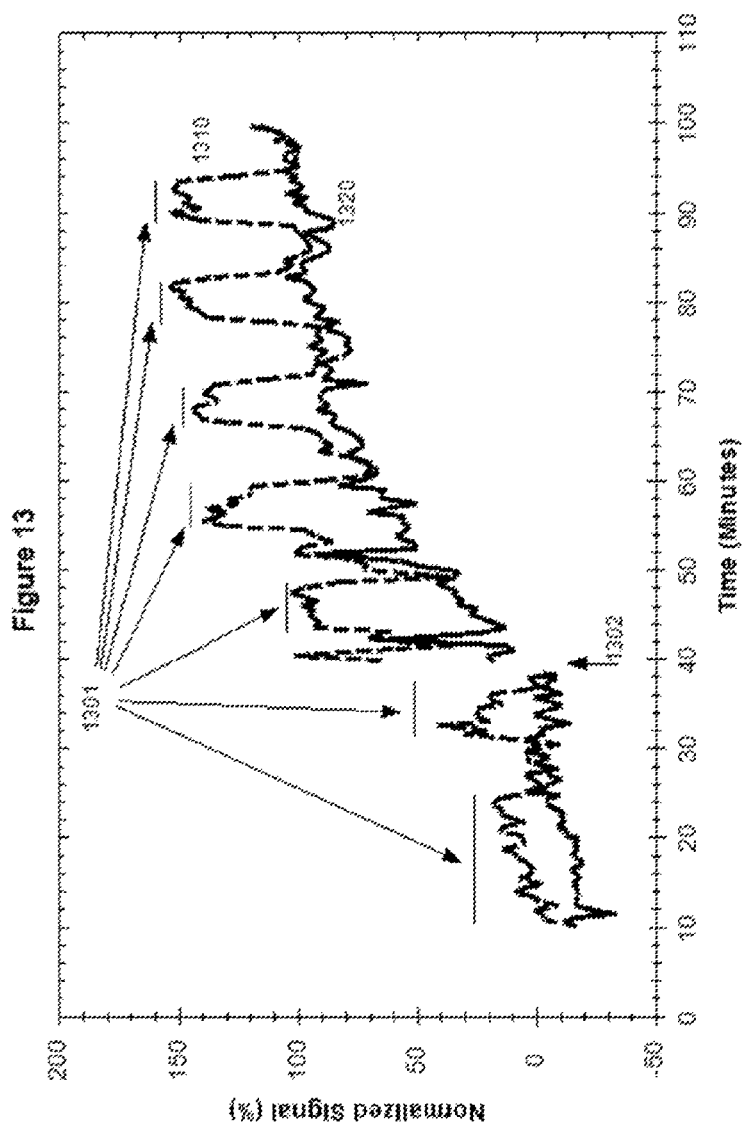

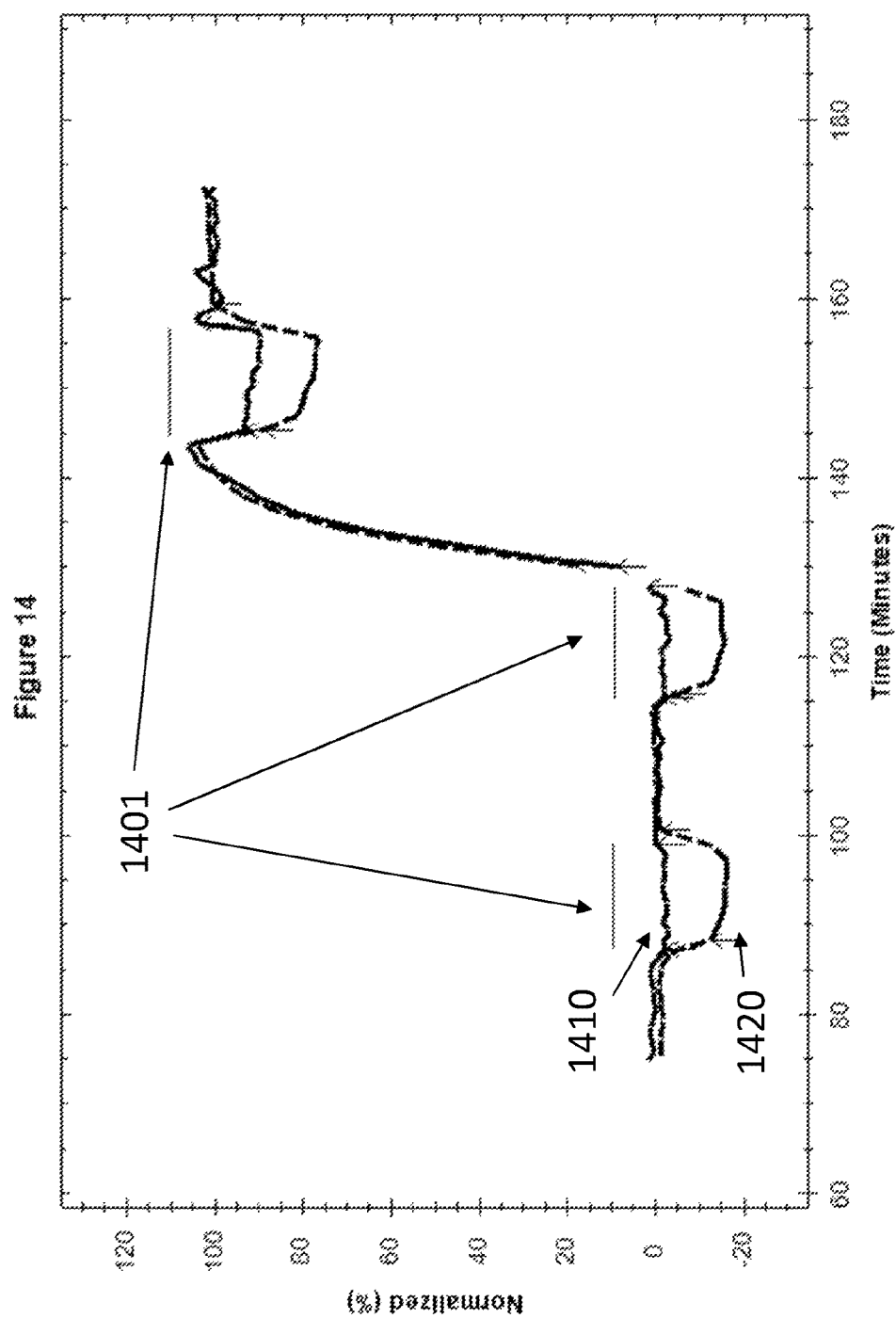

SOLID SUPPORT FOR IMPROVED DETECTION OF INTERACTION BETWEEN SPECIES

This invention relates to a solid support suitable for improving the detection of how different species interact with each other. In more particular, the invention relates to a solid support for use in analytical instrument that rely on a detection principle comprising a reduction of liquid near an area during the course of measurement of said area. Even in more particular, the invention relates to improving the detection of how a molecule (a small chemical structure or a macromolecule like a protein) interacts with a different molecule, where one of the molecules is attached to the solid support.

BACKGROUND OF THE INVENTION

There are numerous methods and devices available for the detection of how different species interact. In the field of biochemistry, one common measurement is to determine how strong an antibody interacts with an antigen, so as to better understand immunological processes. In drug discovery, similar measurements are conducted to determine how strong a small molecule is interacting with a disease-related target, so as to better understand if the small molecule is worth further investigations as a potential drug.

One particular type of method and device for measuring the interaction of different species is disclosed in WO2005080967, which is incorporated by reference herein. Such a device, currently commercially available under the trade name LigandTracer, is capable of measuring interactions between a range of species. In WO2005080967, it is described that the device can measure how a radiolabeled protein interacts with living adherent cells. In the scientific literature there is currently examples of such a device monitoring interactions between virus in suspension and adherent cells, between suspension cells and adherent cells, between small molecules and adherent cells, between proteins in solution and proteins adsorbed to magnetic beads which in turn are anchored through a permanent magnet, and the dissociation of chemicals from solid nanoparticles, to mention a few illustrative examples.

Generally, the device according to WO2005080967 is a device suitable for detecting interactions between species attached to or positioned on a solid support (targets) and species in a liquid (ligands), when said solid support and said liquid are brought into contact. On the solid support, a first species (target) can be attached in one or more non-overlapping defined areas. There is a detector capable of detecting an interaction between said species attached to the solid support, and said species contained in said liquid. The device is characterized by a mechanism adapted for temporarily reducing, in a defined area of said solid support, the amount of liquid with which said support is brought into contact in the course of a detection; and at least one of the defined areas do not have a species of interest attached, so as to form a reference area for the detection. Preferably the solid support as described in WO2005080967 is an essentially flat dish capable of holding a liquid confined within its boundaries, such as a Petri dish, although any other kind of receptacle or vessel capable of confining liquid is possible. The detector could for example be a scintillation detector or a fluorescence detector, although many other types of detectors are possible. The device is connected to a computer for synchronizing detector output with solid support orientation. The key feature in the invention in WO2005080967 is that the amount of liquid covering the defined portion of the support is temporarily reduced prior to performing said measurement. The temporary reduction of liquid comprises a reduction of the amount of liquid near at least one of said defined areas without changing the total amount of liquid in contact with said solid support. A reference measurement is performed on a different portion of the solid support where no interaction takes place, said portion defining a reference area. Suitably, a difference between target and reference measurements is calculated. The sequence of steps of exposing, measuring and reducing the amount of liquid is preferably repeated approximately once every minute, and the concentration of said ligand is increased by a finite amount before said sequence of steps is repeated.

One method for achieving the reduction of the amount of liquid is by orienting the support at an angle that deviates from the horizontal to provide an elevated part and a lower part of said support, such that the elevated part will be covered by less liquid than the lower part, and wherein the support is rotated at a predetermined speed. An alternative method for achieving the reduction of the amount of liquid is achieved by tilting a solid support back and forth.

The solid support as described WO2005080967 in is typically a container. In this container two or more defined areas are present. One liquid put in the container and said liquid contacts all defined areas. At least one defined area is always reserved for reference purposes. The attachment of target on defined areas can be performed in a variety of ways. Cells could be grown directly on a defined area. The defined areas could be coated with a protein known to enhance attachment of cells. The defined areas could be coated with a protein known to bind a specific molecule which is used for attachment of the target. One such protein is streptavidin which binds biotin strongly. A biotinylated target (e.g. biotinylated DNA) could then be conveniently attached as target to the defined area. The surface of the defined areas could be chemically modified to make possible covalent attachment of a target. Passive adsorption of target directly onto the defined area is also possible. The surface of the defined areas is not necessarily solid and flat. Porous surfaces or surfaces with biopolymers attached (e.g. polyethylene glycol or dextran) could be advantageous due to increased target density making a higher signal possible.

In "Biochemical and Biophysical Research Communications 428 (2012) 74-79" there is disclosed that a permanent magnet can be placed under a defined area to anchor magnetic particles in the defined area.

The current LigandTracer® device is designed for attaching one or more species (one or more targets) to a solid support and to keep the other species (or ligand) in solution or suspension. Currently, regular Petri dishes are used as solid support.

SUMMARY OF THE INVENTION

The present invention comprises a development of a novel solid support with features that extend the possibilities to measure interactions between species in a device similar to the one described in WO2005080967.

In a first aspect, a solid support device for use in measurements of the interaction of two different species is disclosed. The device comprises at least one compartment, each compartment being capable of holding liquid within its boundary. Furthermore, each compartment comprises at least two non-overlapping defined areas, at least one of which is designated as a reference area. The solid support is characterized in that the defined areas within one compartment are separated by means of dividers that provides a barrier to fluid flow from one defined area to another when the solid support is placed in a horizontal position, but the dividers are being configured for allowing fluid flow from one defined area to another when the solid support is placed in a non-horizontal position.

In one embodiment, the solid support device further comprises at least two independent compartments.

In another embodiment, the dividers of the solid support device are elongated ridges extending within a compartment so as to subdivide the compartment in equally sized partitions.

In still another embodiment, the solid support device has an elevated part in the center of the device and dividers that extend from the periphery of the device to said elevated part.

In yet another embodiment, the solid support device further comprises non-evenly spaced grooves on the outer side of the support adapted to mate with corresponding pins on a holder, whereby said the device is attachable to said holder in only one way.

In still another embodiment, the dividers in the solid support device are made of solid material.

In yet another embodiment, the dividers in the solid support device are provided as hydrophobic areas between the defined areas.

The dividers in the solid support device may further be made of a material capable of shielding the emission of a fluorescent or radioactive label, or comprise a slit for housing a shielding material. An identity structure may further be placed on to the exterior of the solid support device.

In a second aspect, a method of detecting interactions between species on a solid support and species in a liquid is disclosed. The method comprises a solid support with at least two independent containers, each of the containers having at least two non-overlapping defined areas. A first species is attached on at least one of the defined areas. At least one defined area is an area of the solid support where no species of interest is attached to said portion defining a reference area. The detection of interactions comprises, for each defined portion in each container, exposing the defined portion to a liquid containing a second species, so as to cover the defined portion of the solid support, thereafter temporarily reducing the amount of said liquid being in contact with the defined portion holding said first species, the reduction being carried out so the amount of liquid that remains on the defined area is less than 10% of the amount of liquid present in the vicinity of the defined area when the solid support is positioned horizontally in rest, and finally performing a measurement capable of detecting an interaction between said first and said second species of the defined portion covered with a temporarily reduced amount of liquid. The steps of exposing to liquid, reducing the amount of liquid, and performing a measurement are repeated so as to produce a time-resolved measurement and the temporary reduction of liquid comprises a reduction of the amount of liquid near at least one of said defined areas without changing the total amount of liquid in contact with any of said containers in said solid support. The temporary reduction of liquid is provided by rotating the solid support which has an orientation deviating from the horizontal such that a portion of the solid support at any time is immersed in said liquid, and the solid support is rotated more than 120 degrees between each detection.

DESCRIPTION OF THE DRAWING

In order that the invention may be more clearly understood, the preferred and alternative embodiments thereof will now be described in detail by way of example, with reference to the accompanying drawing, in which:

FIG. 9 shows the assembly of multiple solid supports of the type described in FIG. 8;
FIG. 12 shows a suitable solid support and results from a measurement conducted using two independent liquids in the same solid support.
FIG. 13 shows a suitable solid support and results from a measurement conducted using two independent liquids in the same solid support, when altering the rotation scheme.
FIG. 14 shows the obtained signal, presented for each compartment as signal from the defined reference area subtracted from the signal from defined area holding target

DETAILED DESCRIPTION OF THE INVENTION

Figure 1:
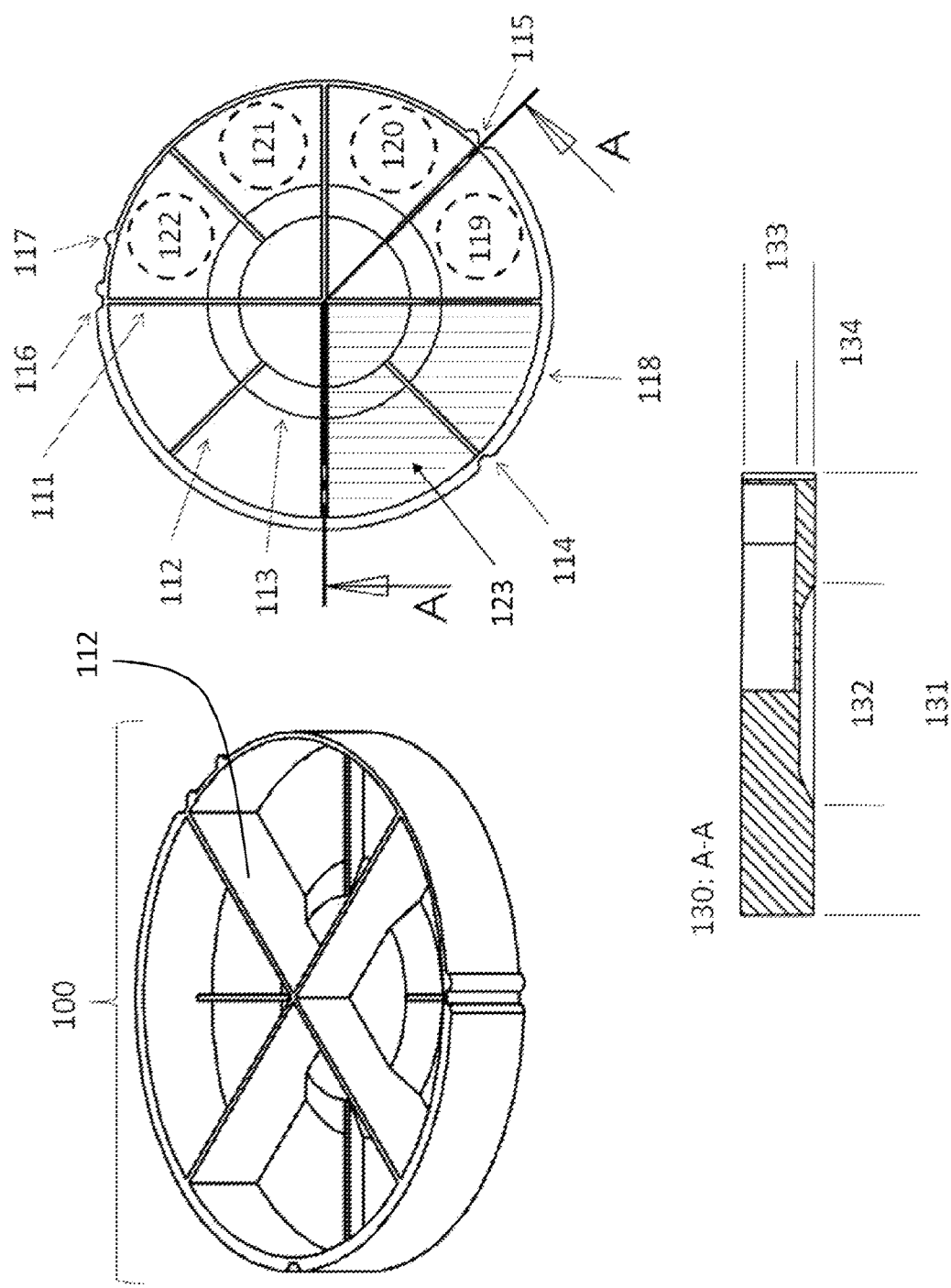
FIG. 1 shows a suitable solid support.

For the purpose of this application, and for clarity, the following definitions are made:

Horizontal position is defined 5 degrees slope or less from nominal horizontal, and inclined is defined as more than 5 degrees slope.

A species that is attached to the solid support is denoted "target" or "first species" and a species present in a liquid is denoted "ligand" or "second species". Possible species (i.e. targets and ligands) include, but are not limited to, tissue samples, cells, bacteria, viruses, solid particles, macromolecules (e.g. proteins, DNA, RNA) and other chemical compounds. Preferred ligands include macromolecules (e.g. proteins, DNA, RNA), other chemical compounds and any species that can be dissolved in a liquid.

Solid support is defined as an essentially flat dish capable of holding one or more liquids confined within its boundaries, such as a Petri dish, although any other kind of receptacle or vessel capable of confining liquid is possible.

A compartment is defined as a container which can hold exactly one liquid confined within its boundary. In general a prior art solid support has at least one compartment. Solid supports according to the present invention have two or more compartments.

Defined area is defined as a local area or region of a compartment, where each defined area is covering less than 50% of the compartment area. A compartment has at least two non-overlapping defined areas. At least one defined area is reserved for attaching a target (also referred to as an active area) and at least one defined area is reserved for reference purposes. A reference area either has nothing attached to it or has an irrelevant target attached to it.

The present invention aims at improving the efficiency of the characterization of interactions between different species. In particular, the present invention aims at improving the efficiency of the characterization of interactions between different species in cases when a device similar to the one described in WO2005080967 is used.

The device described in WO2005080967 is capable of detecting interactions between species attached to a support (targets) and species in a liquid (ligands), when said support and said liquid are brought into contact. There is a solid support on which a first species can be attached in one or more non-overlapping defined areas thereon; a detector capable of detecting an interaction between said species attached to the solid support, and said species contained in said liquid. The device is characterized by a mechanism adapted for temporarily reducing, in a defined area of said support, the amount of liquid with which said support is brought into contact in the course of a detection; and at least one of the defined areas do not have a species of interest attached, so as to form a reference area for the detection.

In order for a solid support to function in the context of the device described in WO2005080967, said solid support should be essentially flat, and has to be capable of holding a liquid confined within its boundaries. The solid support must further comprise at least non-overlapping defined areas, at least one such defined area of which is used for reference purposes. The device will, according to WO2005080967, temporarily reduce the liquid near a defined area during the detection of presence of labeled species in said defined area. One possible method for achieving a temporarily reduced amount of liquid near a defined area is to use a circular solid support and place it on a sloping and slowly rotating support holder, and mount the detector over the elevated portion of the support. By placing the defined areas along the rim of the circular support, each defined area can be placed near the detector through rotation of the support holder, while the majority of the liquid will stay in the lower end of the solid support. Another possible method for achieving a temporarily reduced amount of liquid near a defined area is to use a solid support placed on a tilting platform. During detection, the platform elevates one part of the support wherein multiple defined areas are located in a non-overlapping manner, so as to temporarily move liquid to the lower end. A detector is mounted over the elevated region for the purpose of detecting presence of labeled species on the different defined areas.

The current use of LigandTracer, a device operating according to the principles described in WO2005080967, typically involves the use of two defined areas of which one is a reference. In rare cases, use of three or four defined areas has been disclosed (see for example the report "Real-time immunohistochemistry analysis of embedded tissue" by Lars Gedda and co-authors as published in Applied Radiation and Isotopes 68 (2010) 2372-2376, which is incorporated by reference herein). In all cases, regular petri dishes have been used as solid support and exactly one liquid is in contact with the solid support at any point in time. This can be a limitation because it is sometimes desirable to detect the interaction of different species (or ligands) with a cell line, alternatively the same species at different ligand concentrations, simultaneously. In still other cases, it is desirable to detect the interaction of a greater number of cell lines and multiple different species or multiple different concentrations of one species simultaneously. According to the present invention, it is possible to make solid supports that (a) make the operational procedures for handling multiple defined areas within the same solid support simpler and (b) parallelize measurements, so as to overcome the identified limitations.

The problem to overcome is hence to introduce at least two different, independent compartments each holding different liquid into the same solid support in a manner that can be used in a device operating according to the principles described in WO2005080967 (wherein only one liquid per solid support is described). Technically, there are two issues to overcome. The first issue relates to ability to detect a plurality of molecular interactions occurring on defined areas in each compartment. This can, according to some embodiments of the present invention, be overcome by shaping two containers as half-circles, and connecting them to form one circular solid support structure, and then detect along the rim of the solid support during slow rotation in inclined orientation. However, the fact that the two compartments are non-symmetrical with respect to the rotational axis of such a solid support introduces another problem, namely obtaining even drain of liquid from the defined area before detection. Even drain can however be obtained through redesign of how the solid support is rotated prior to measuring, according to the present invention.

In FIG. 1 a novel solid support suitable for the use in a LigandTracer-like instrument is shown. The support 100 is a circular Petri dish like container, i.e. having a generally circular geometry such that each compartment has the shape of a circular segment.

The dish has an essentially flat bottom except for the center of the dish, where the bottom may be elevated. The dish contains two types of dividers. There are first (high) dividers 111 for the purpose of separating liquids, i.e. to make it possible to use completely independent liquids in different compartments in the same solid support. One compartment is indicated as a striped area 123. Each area limited by said first (high) dividers has at least one second (low) divider 112. The purpose of the second (low) divider is to simplify the separation of the defined areas when the solid support is placed in horizontal position. The optional center elevation 113 makes it possible to reduce the size of the defined areas. When placing the dish in a horizontal position, different liquids can hence be placed in the local compartments limited by low dividers and the center elevation. Typically, the second (low) dividers of the solid support are elongated ridges extending within a compartment so as to subdivide the compartment in equally sized partitions. In a local compartment, there is typically one defined area. The local compartments should, when placed at horizontal position, hold at least 10 microliter and at most 30 milliliter of liquid. In the current format of LigandTracer® instruments, each local compartment should hold between 50 microliters and 1 milliliter of liquid depending on the size of the defined area. In general, it is preferable to engineer the solid support so that each local compartment has barriers capable of holding an approximately 0.3 mm thick evenly distributed liquid layer in place. It is even more preferable to engineer the solid support to hold a 1 mm thick liquid layer, or even a 3 mm thick liquid layer, or 10 mm thick. This means that e.g. cells of different types can be cultivated in the different local compartments, or different proteins can be adsorbed to the surface of the bottom of the different local compartments.

When placed in a device similar to a LigandTracer® device, the dish will rotate slowly at inclined orientation with a detector being mounted over the elevated portion of the solid support. In the lower position at inclined orientation, the second (low) dividers are low enough to allow the liquid to contact all defined areas separated by said low barriers. In the exemplary solid support depicted in FIG. 1, each container is prepared for two defined areas. For two of the containers, the defined areas are illustrated with a dotted circle 119, 120, 121, 122. Within each compartment, there must be one defined area for reference use and another one having a species of interest attached. All defined areas irrespective of which compartment they belong to are typically located at approximately the same distance from the center of the circular solid support. The dish may optionally have gaps or grooves or other geometrical structures 114, 115, 116, placed in a non-regular pattern on the outer perimeter so that the solid support can be placed in a holder in exactly one orientation.

If the device utilizing the solid support is equipped with a solid support holder comprising three pins oriented to fit in grooves 114, 115, 116, then it will be possible to place said solid support in said holder in exactly one way. More generally, the solid support can have any number of non-evenly spaced grooves or non-symmetrical geometrical patterns on the outer side of the support adapted to mate with corresponding pins or structures on a holder, whereby the solid support is attachable to the holder in only one way.

The solid support may optionally have an identity feature, which makes it possible to detect which type of dish has been placed in the dish holder. Such an identity feature could be mechanical in the form of a ridge 117 which can be sensed by a mechanical switch or an optical switch.

The ridges are provided on the outer periphery of the solid support structure, but in order to provide a "nominal" diameter, the wall 118 has been made thinner in the region where the ridges are provided. Thus, the ridges extend from the periphery to an extent corresponding to the outer diameter of the solid support as a whole.

By placing the ridge 117 at different locations between groove 115 and groove 116, the identity of the dish can be represented through the location of the ridge. By using multiple identity features, a digital signature could be incorporated on the solid support. For example, using eight such identity feature ridges would allow 256 unique combinations (one byte of information). It is also possible to attach a barcode on the outer side of the solid support to make optical identification of the solid support possible. Using a solid support like the one described in FIG. 1 in a LigandTracer-like device will result in the possibility of conducting multiple independent measurements simultaneously.

The approximate dimensions of the solid support depicted in FIG. 1 are described using the cross section sketch 130, which describes the section defined as A. The approximate dimensions are the following:

| | |
|---|---|
| Outer diameter OD (131): | 30-300 mm |
| Center elevation diameter CD (132) | 0-0.95 * OD |
| Solid support height SH (133) | 3-50 mm |
| Center elevation height CH (134) | 0-0.7 * SH |

The height of the high dividers is similar to SH and the height of the low dividers is typically similar to CH, but can be higher.

In a general sense, the solid support shown in FIG. 1 is an essentially circular solid support comprising more than one compartment, said compartments being distributed in a regular manner with respect to the rotational axis, said compartments having essentially identical geometry and each compartment is non-symmetric seen alone from the perspective of the rotational axis. This means that liquid present in one compartment will move in different patterns inside said compartment depending on if said compartment is rotating from the lower end towards the elevated end, or in the other direction. Uneven liquid motion pattern may result in difficulties during detection, as described below, but these difficulties can be overcome by use of the present invention.

Figure 2:
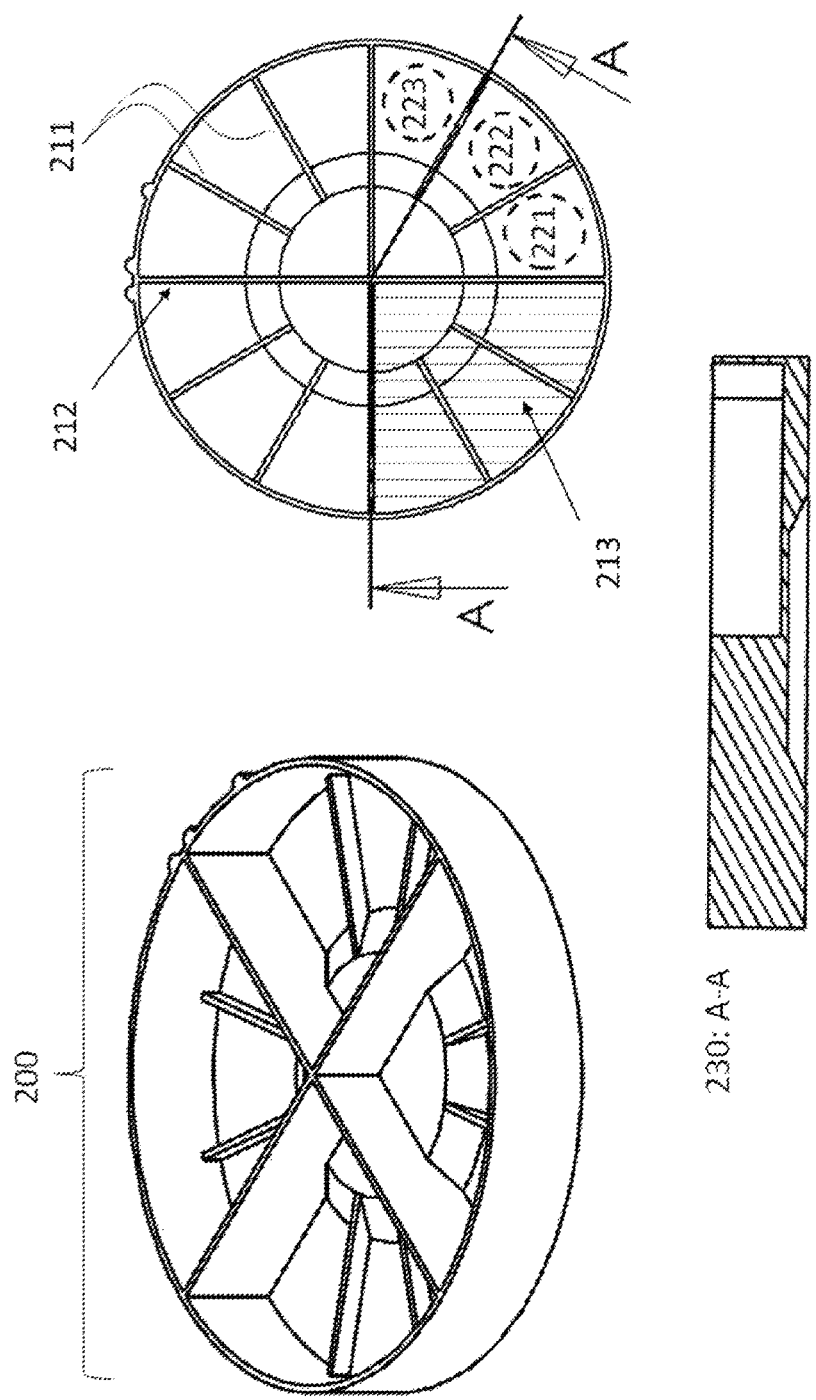
FIG. 2 shows a suitable solid support.

The solid support as described in FIG. 1 can be modified to include different numbers of compartments (from one compartment to more than 100 compartments), wherein each compartment is divided into at least two local compartments. In FIG. 2, another non-limiting example is shown. The solid support 200 has four compartments (one of them illustrated as a striped area 213), the compartments being separated by first (high) dividers (one of them indicated as item 212) and each compartment has two second (low) dividers 211 per compartment dividing each compartment into three defined areas 221, 221, 223. A cross section image 230 describes the section defined as A. This type of solid support would make it possible to conduct four independent measurements, each using one reference area and two defined areas containing potentially different species of interest.

Figure 3:
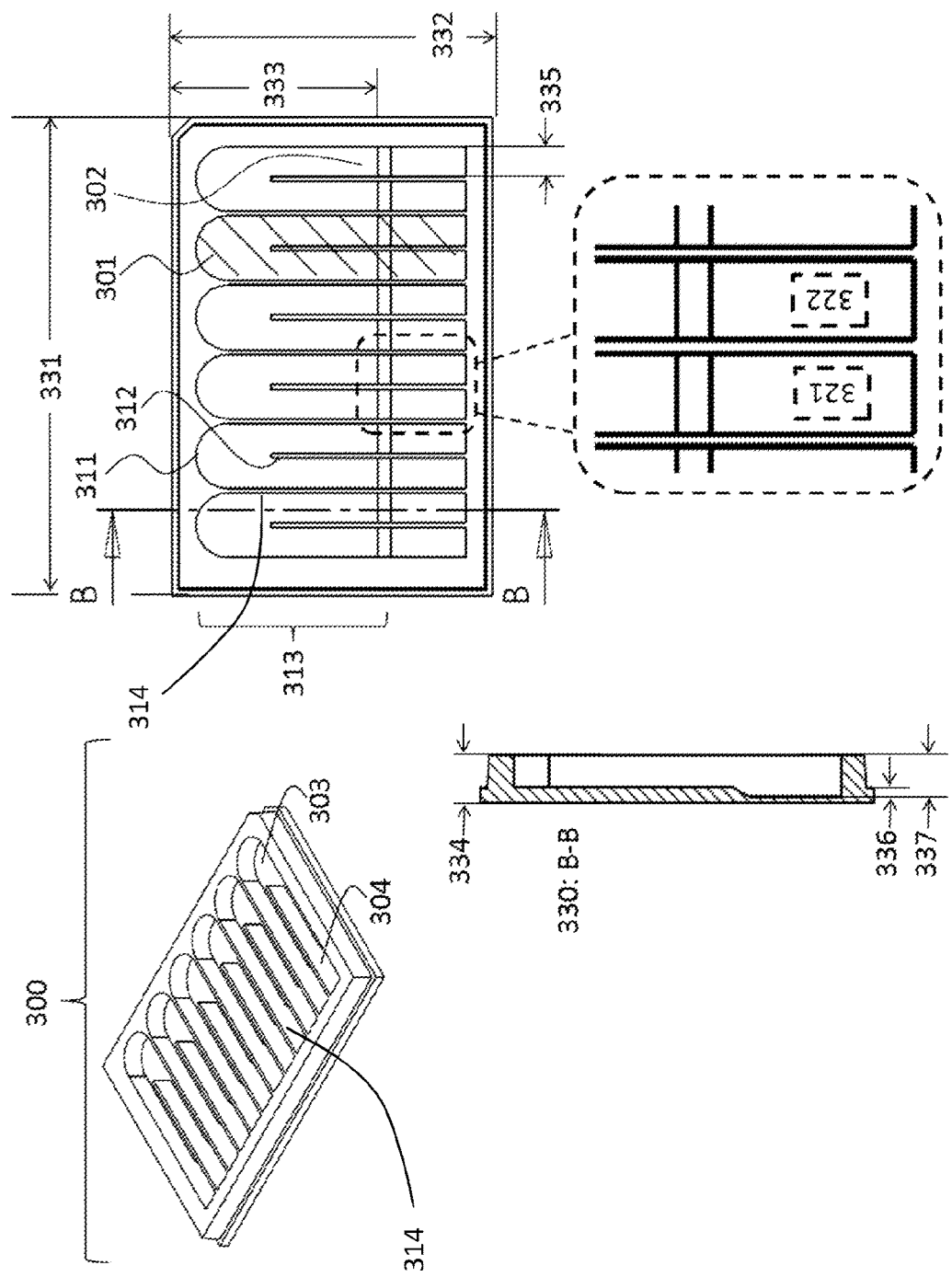
FIG. 3 shows a suitable solid support.

In FIG. 3, a completely different type of solid support 300 is shown. The non-limiting, exemplary support 300 has the approximate geometry of a microplate. For comparison, a microplate has the approximate dimensions 128 mm*85 mm*15 mm. Thus, the present device has a generally rectangular geometry.

Figure 4:
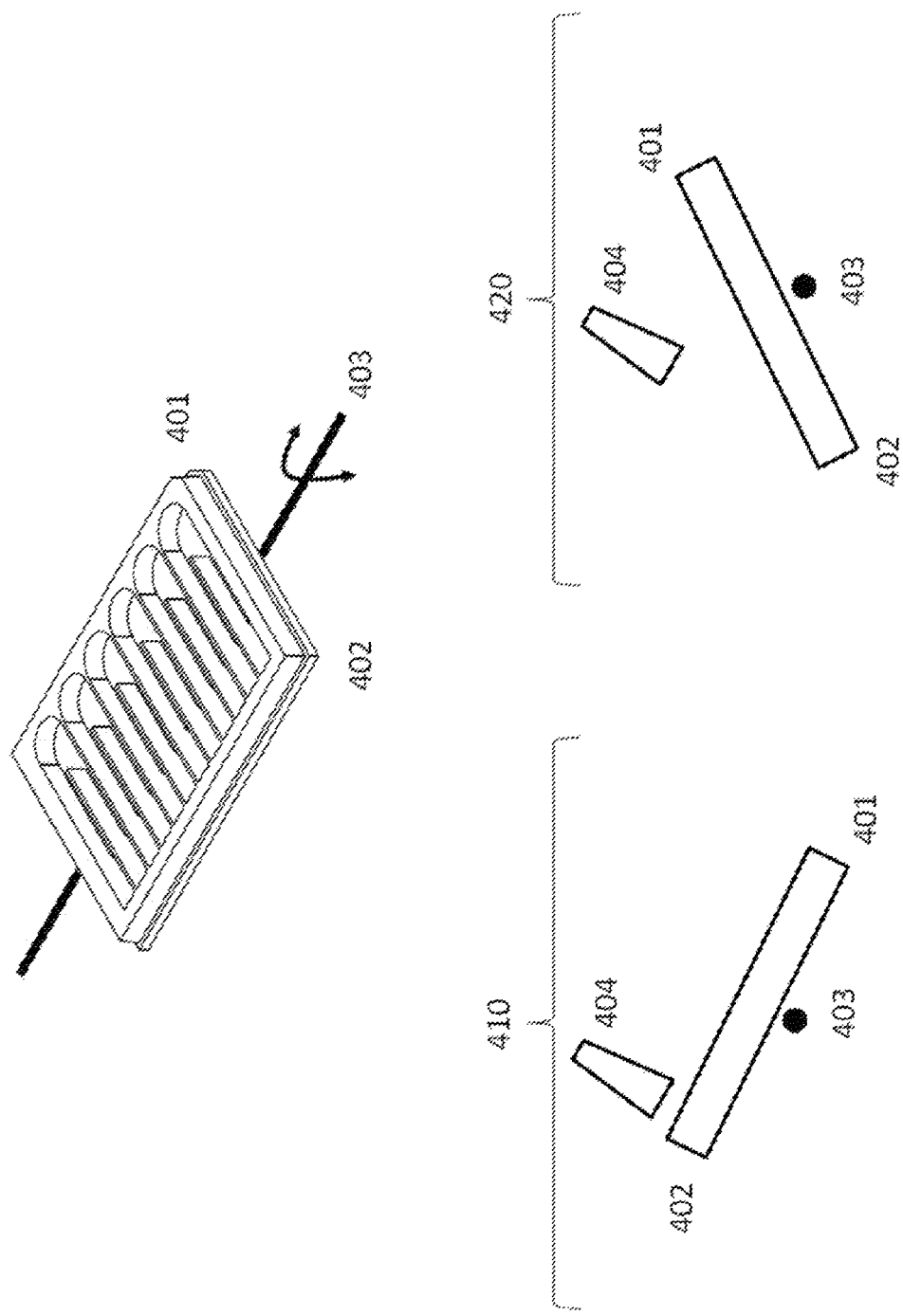
FIG. 4 shows how the suitable solid support 300 could be oriented in a measurement device.

The support in FIG. 3 has six compartments (one of them dashed as item 301) suitable for use in a device according to WO2005080967 using the previously described tilting method for temporarily reducing the liquid during detection. The compartments are elongated and extend across the device, and there is an elevated region 333 at one end of each compartment. Each such compartment has an outer perimeter 311 and first (high) dividers 314 separating the compartments 301, and at least one second (low) divider 312, where the divider separates the compartment into two elongated "blind" arms (one arm being displayed as item 302), the arms being "blind" in the sense that said arms are in fluid communication at one end 303, and have a dead end 304 in the opposite end. It should be noted that although these dividers are shown to be essentially the same height as the dividers 314 separating the respective compartments, they need only be high enough to provide a barrier to fluid flow between the defined areas during preparation of said areas (compare description relating to FIGS. 1 and 2). Each arm contains one defined area 321, 322, located in the end without connections. The support has an essentially flat bottom with the exception of a slightly elevated area 313 in the region where the arms are connected. When placed horizontally, different liquids can be placed in the different arms, being held apart by the elevated bottom near the arm connection. This makes it possible to cultivate different cells in the different arms at the defined areas. It is however possible to use a solid support of this type without the elevated area 313, but that requires that the cultivation of cells is conducted with the solid support slightly tilted so as to keep the area where arms connect slightly elevated and liquid in the different arms separated. When placed on a regularly tilting table, liquid will gather in the connection point when the connection point is in the lower end, providing one homogenous liquid in the complete compartment while at the same time reducing the amount of liquid in the elevated non-connected arms where detection is conducted. This is illustrated in FIG. 4, where the axis of rotation 403 can result in elevation of the defined area end 402 or elevation of the arm connection end 401. A detector 404 capable of detecting presence of species in all defined areas is mounted near the "dead" end 402 of the solid support when the dead end is elevated, see 410. Liquid is then returned to the defined area by elevating the arm connection end 401 as illustrated in 420. The approximate dimensions of a solid support of the type illustrated in FIG. 3 are the following:

Length LE (331): 30-300 mm
Width WI (332): 0.1-1.0*LE
Elevated region ER (333): 0-0.8*WI
Total height TH (334): 3-50 mm
Elevation height EH (336): 0.1 mm-0.9*CD
Compartment depth CD (337): 0.1-0.9999*TH When tilting the support back and forth, the homogenous liquid in a compartment will contact all connected arms within the compartment while the liquid will be temporarily reduced during the course of detection. It is possible to make supports having different numbers of connected arms within a compartment, and also multiple independent compartments placed in the same solid support. The latter means that during a measurement in a tilting device according to WO2005080967, multiple independent measurements can be conducted simultaneously.

Figure 5:
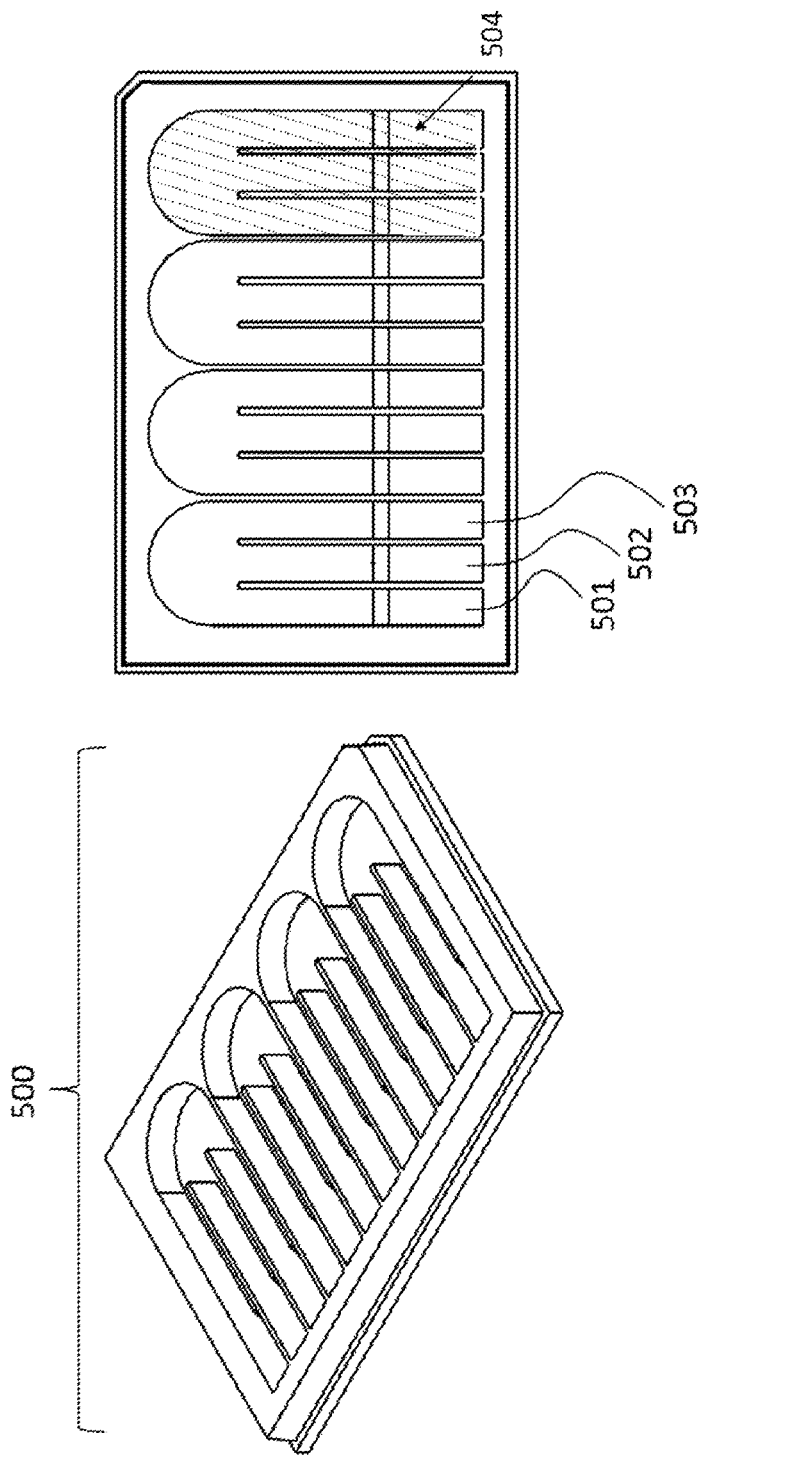
FIG. 5 shows a suitable solid support.

It is possible to use different kinds of similar solid supports of the type illustrated in FIG. 3. One non-limiting alternative is the solid support shown in FIG. 5, wherein a micro-plate like support (500) comprising four compartments (one of them indicated as a striped area 504), each having three arms 501, 502, 503, is shown.

Figure 6:
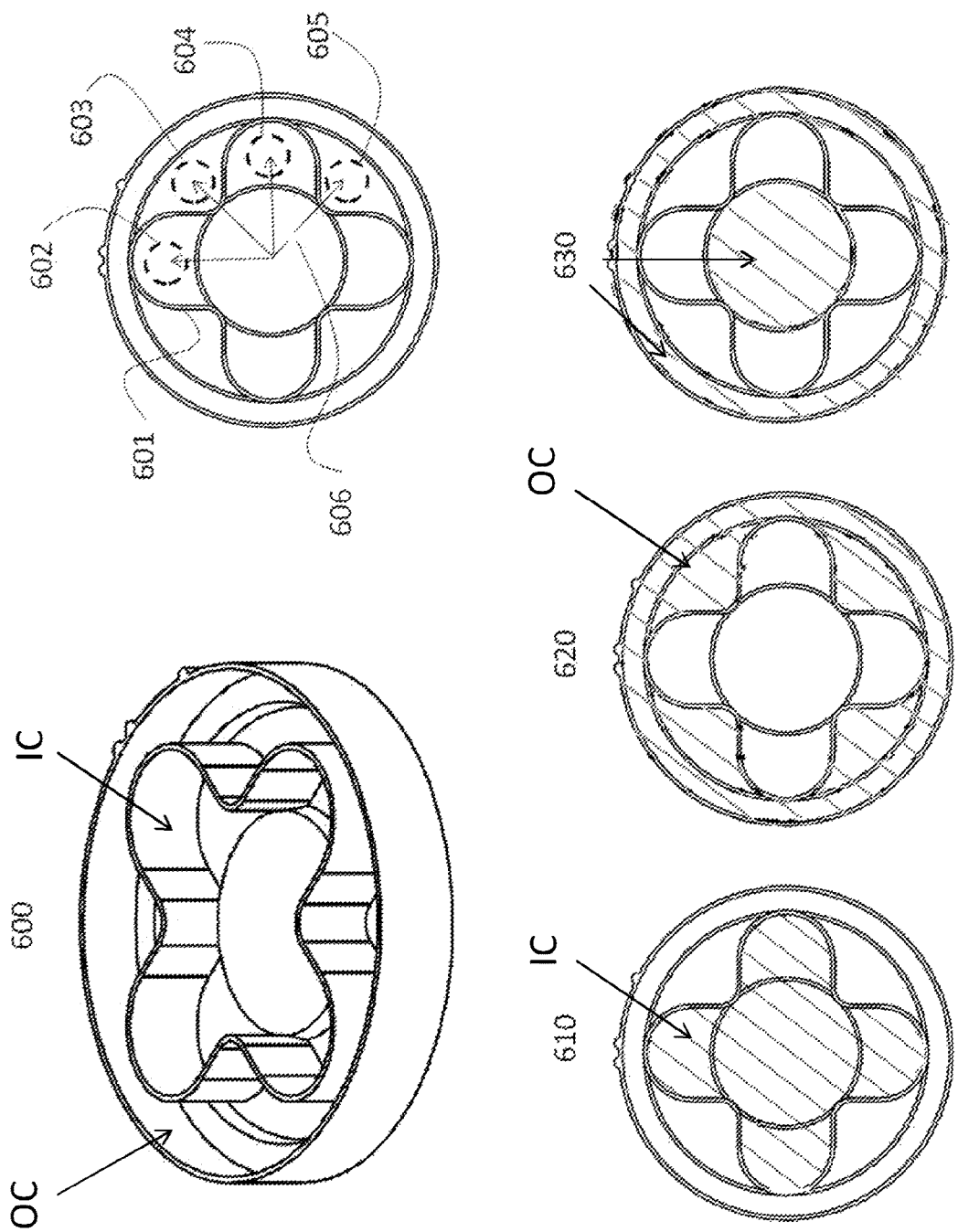
FIG. 6 shows a suitable solid support.

In FIG. 6, still another possible type of solid support 600 is shown. It is a circular, Petri dish like solid support which has two compartments separated by one first (high) divider 601. There is an inner compartment IC with at least two defined areas, and in the case of embodiment in FIG. 6 there are four defined areas two of which 602, 604 are marked with dashed circles. The inner compartment IC is highlighted at 610 as horizontal dashes. There is an outer compartment OC having approximately the same number of defined areas as the inner compartment IC. In the case of the solid support 600 there are four defined areas in the outer compartment OC, two of which are shown as dashed circles 603, 605. The outer compartment is highlighted in 620 as vertical dashes. All defined areas, irrespective of which compartment they belong to, are located at approximately the same distance from the center of the solid support, as indicated with the four arrows 606. To make it possible to use different liquids in the defined areas when the solid support is placed in horizontal position, the outermost portion and the center of the solid support has a slightly elevated bottom, illustrated as dotted areas in 630. In solid supports similar to 600, the effect of the second (low) low dividers discussed for solid supports of type 100 (FIG. 1) is provided by elevated areas 630 connecting to the curvilinear high divider 601, resulting in that the defined areas (exemplified as 602-605) are delimited from each other within the respective compartments. The region between the elevated areas where all the defined areas are located have an essentially flat bottom.

Figure 7A:
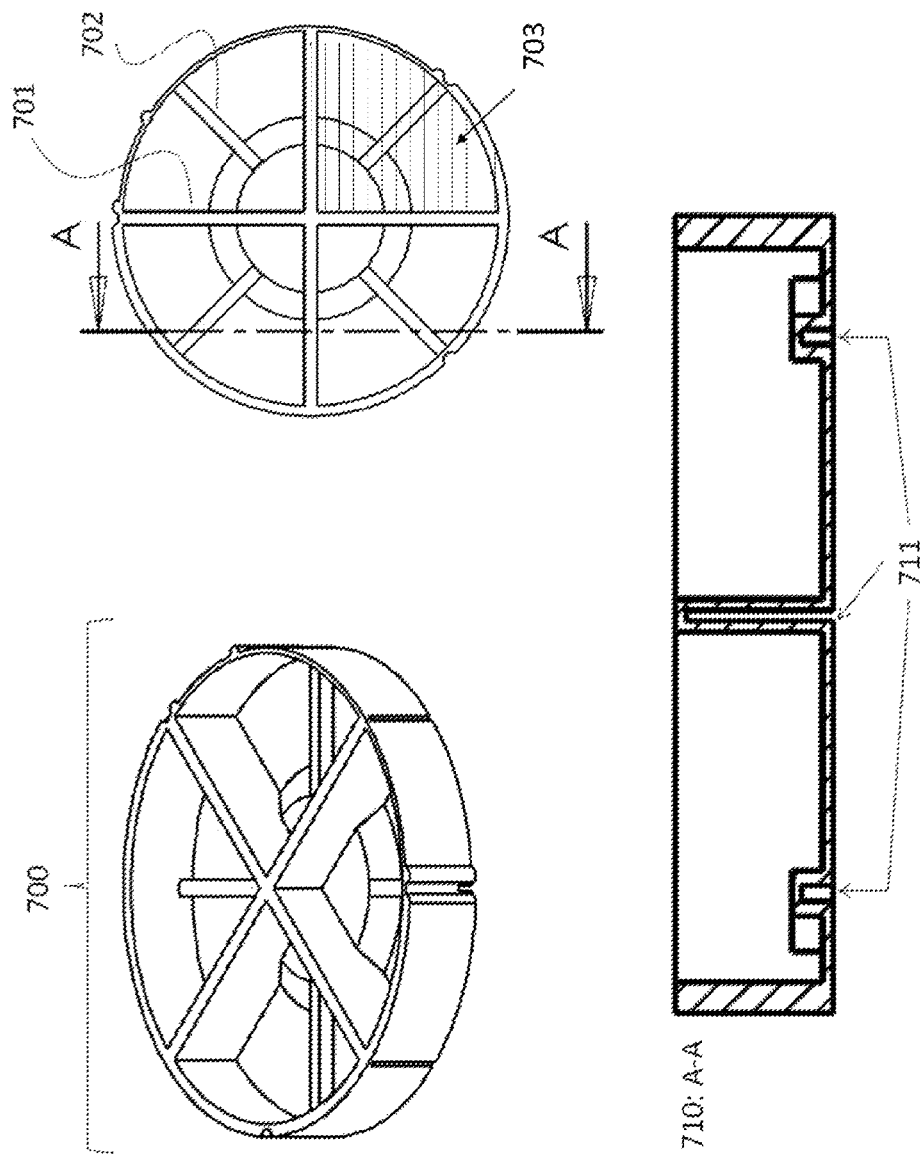
FIGS. 7A and 7B show a suitable solid support.
Figure 7B:
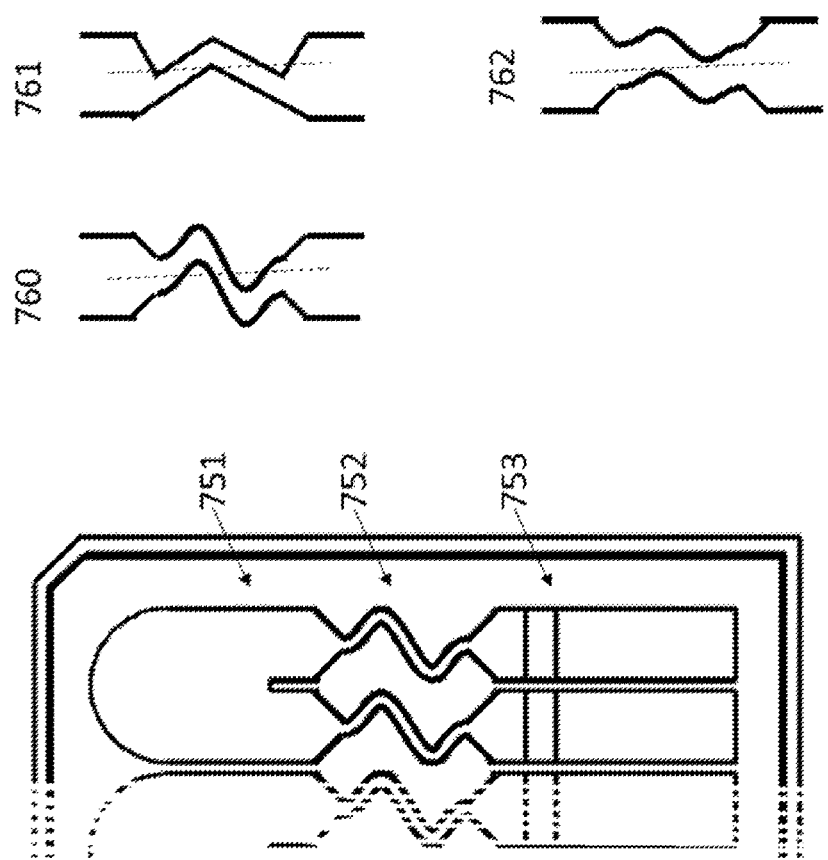

The method and device of WO2005080967 is often configured to use at least one labeled species. The label is commonly a radioactive label or a fluorescent label. During the course of detection of labeled species in one defined area, the detector may need to be shielded (or collimated) from signal originating from any other defined area. Currently used shielding is typically mounted on the detector. It is however possible to integrate shielding in the solid support to improve the total shielding. One possible method to improve shielding in the case of radioactive labels is to include metal ridges on the solid support holder. The solid support can be equipped with grooves where said metal ridges fit. For optical detection methods like fluorescence detection it is possible to use a non-transparent material to block stray light, mounted in a similar manner as for the metal shielding. One possible solid support where the possibility to shield the defined areas in circular solid supports is shown in FIG. 7A. The solid support 700 is similar to the one shown in FIG. 1, with the exception of the dividers. Both the high dividers 701 and the low dividers 702 are wider, but the compartments (one illustrated in the striped area 703) are the similar to the support in FIG. 1. As shown in the view 710 as a section along the line A-A, the dividers have a groove or slit 711 where a suitable shielding may be fitted. It would in theory be possible to manufacture the complete solid support in a shielding material, but this is often not desirable. In cases when the support is used for cell culturing, it is desirable to use a transparent material so that the cell culture can be investigated in a conventional microscope, which makes it less attractive to use black plastic to shield fluorescence emission from unwanted areas in the complete dish. Some shielding materials are further toxic, for example lead that is commonly used for radioactivity shielding would not be compatible with cell culturing due to the toxicity of lead. A similar type of collimation can be included in a rectangular solid supports intended for a tilting device suitable for solid supports (like the ones shown in FIG. 4 and FIG. 5). In such a configuration, illustrated in FIG. 7B, the end where fluids are connected 751 is connected to each dead-end arm 753 through a curvilinear channel 752. The curvilinear channels need to be configured to block any ray of light or radioactivity. Curvilinear channel design 760 and 761 are both designed to prevent any ray (indicated by the dotted line) from passing through the channel. Curvilinear channel 762 will NOT function, because there is an unshielded way through the channel.

Figure 8:
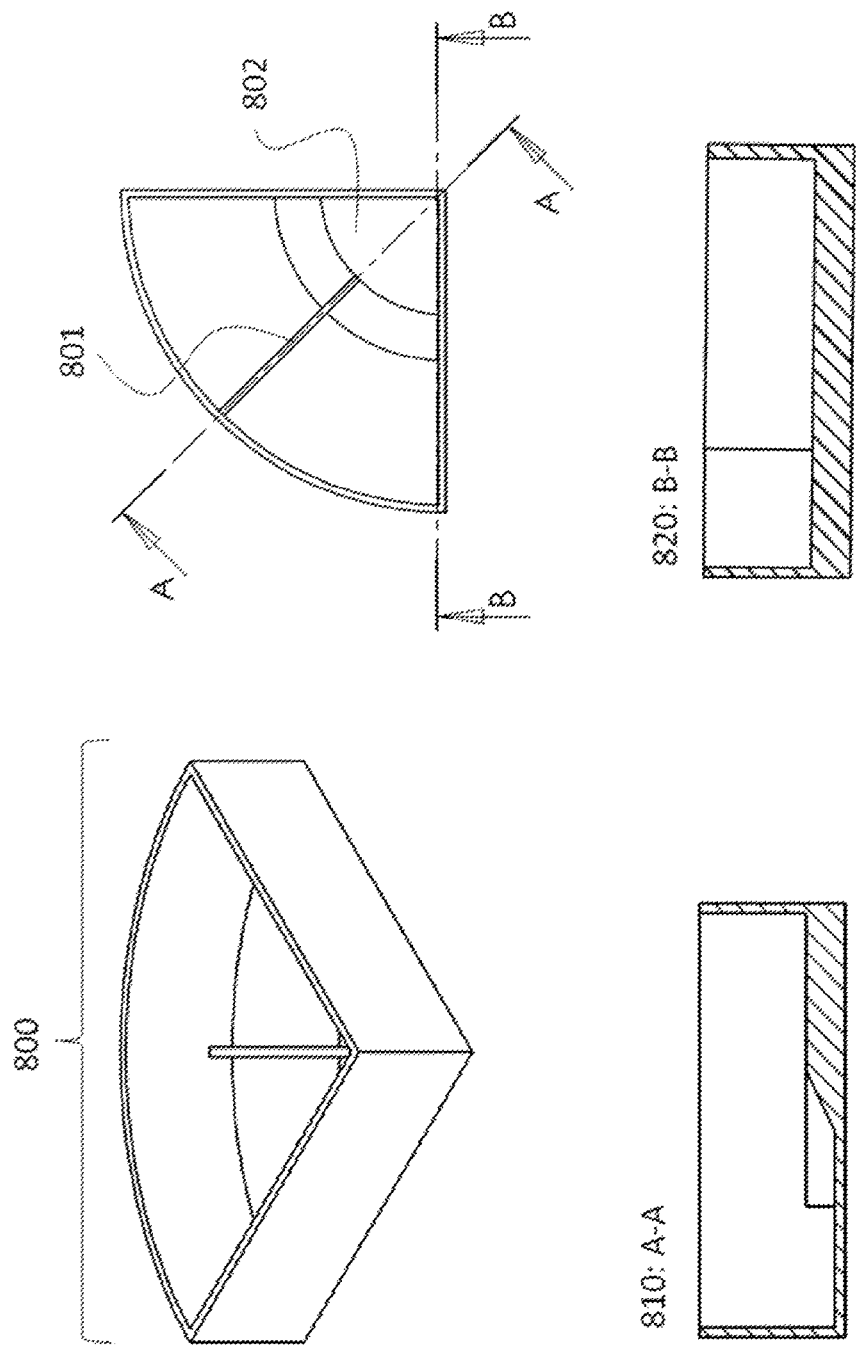
FIG. 8 shows a suitable solid support.

Another example of a suitable solid support is shown in FIG. 8. The exemplary solid support 800 is one compartment of the solid support illustrated in FIG. 1. Hence, the solid support 800 is a sector of a circular support, wherein multiple sectors together form a circular unit, in the case of 800 four such solid supports. The solid support 800 has at least one low divider 801, may optionally have high dividers, and optionally a center elevation 802. The dimensions are similar to the ones disclosed for the embodiment of the support 100 shown in FIG. 1. The section views along the line A-A 810 and B-B 820 are provided for clarity. When using the support 800 in a LigandTracer-like instrument, multiple supports are placed simultaneously in the instrument. As illustrated in FIG. 9, four supports 901, 902, 903, 904 of type 800 would be required for completing a circular assembly of solid supports on a solid support holder 911 which is shown in the view 910 where the solid support 904 has been slightly moved to enhance visibility.

The dividers in the solid supports are typically physical dividers made of the same material as the rest of the solid support. It is however possible to manufacture dividers in a shielding material. Furthermore, since the purpose of the low dividers is to separate liquid on the different defined areas when the solid support is placed in horizontal position, the low dividers need not be wall-like solid dividers. It is for example possible to use a hydrophobic divider, such as a printed silicone pattern, which separates the liquid on the defined areas through differences in surface tension instead of using a physical barrier. When tilting a solid support with hydrophobic dividers, the amount of liquid near the lowest end of the support is large enough for gravity to force the liquid across the hydrophobic barrier, and hence make the hydrophobic barrier to work like a solid barrier.

Figure 10:
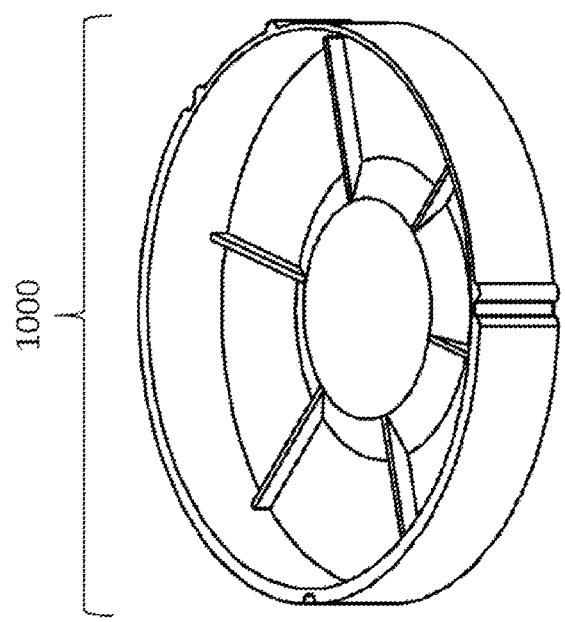
FIG. 10 shows a suitable solid support.
Figure 11:
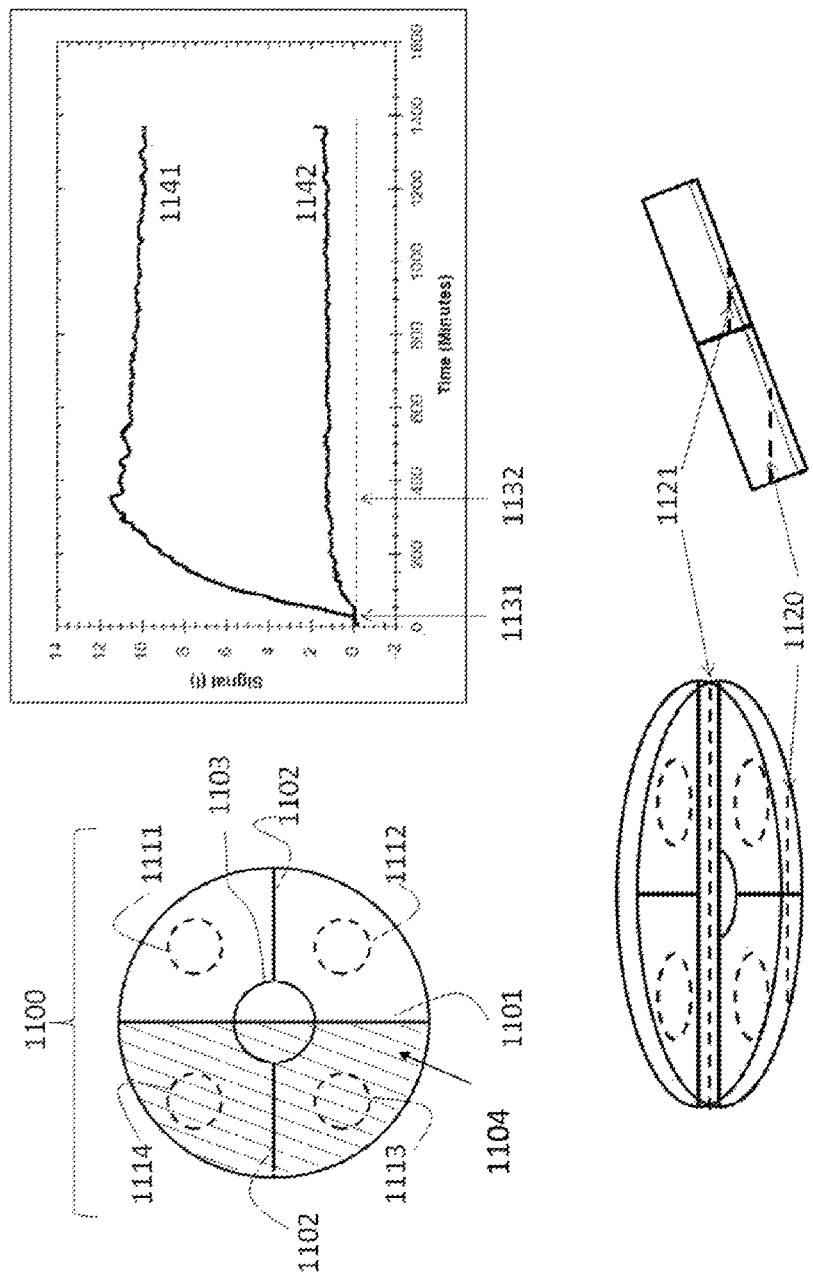
FIG. 11 shows a suitable solid support and results from a measurement conducted using two independent liquids in the same solid support.

All solid supports described in the present application, with the exception of the solid support 600, can have any number of dividers, compartments or containers. It is for example possible to use a solid support 1000 with only low dividers as exemplified in FIG. 10, which has one compartment suitable for use of multiple species (in the case of 1000 it is 6 defined areas). The typical solid support will however have 1-6 independent compartments, and each independent compartment may have 2-100 different defined areas separated by low dividers in a manner that allows separation of liquid in each independent compartment when the solid support is placed in a horizontal position, but which allows for the liquid in a compartment to mix when the solid support is placed in an inclined position. The solid support of the type illustrated in FIG. 6 has exactly two compartments, but the number of defined areas per compartment may vary from 2 to 20.

There are two essential functions of the solid supports described in this patent application. The first of the functions is the one provided by the low dividers. Namely, the low dividers separating the defined areas within a compartment, are high enough to keep liquid separated when placed in horizontal position, but allow liquid from all defined areas in the same container to mix when the solid support is placed in a device for interaction detection and subjected to a tilting action. This simplifies the preparation of the solid support in cases where different cells are grown in different defined areas, or when different proteins are adsorbed to the different defined areas, while making it possible to use one homogenous liquid in the compartment during the assay. For a circular solid support, for example like the one in FIG. 1, it is important that while the low dividers are capable of holding a known quantity of liquid in horizontal position, the same amount of liquid should cross the low barrier at some location when placed in inclined position. Liquid could either cross the low divider when the low divider is at the lowest position when in a sloping and rotating orientation, or when the low divider is at the highest position when in a sloping and rotating orientation where the liquid cross the low divider near the center of the solid support. When combined with a mechanical feature to allow only one orientation, the precise detection of each defined area is made possible, because the geometric relationship between the support holder and the solid support is known, and the device is connected to a computer for synchronizing detector output with solid support orientation. Hence, it is possible to use the known support orientation and the computer controlled rotation to precisely locate each defined area under the detector for detection. For a rectangular solid support, for example like the one shown in FIG. 3, liquid within the same compartment will mix when the part of the solid support where the arms are connected is tilted to a lower end. This feature is essential, because during the measurement of how a first species interact with a second species it is important that the same liquid is in contact with all defined areas within the same compartment. The second essential function is that multiple compartments are made possible within one solid support. The measurement principle in which the solid supports are to be implemented requires that there is one liquid contacting all and at least two defined areas within a compartment, and that the liquid near a defined area is temporarily reduced during the course of a detection. For this principle to hold, there have to be easily separable defined areas within the same compartment.

The temporary reduction of liquid during detection is often simplified when each compartment in a solid support is either essentially symmetric or essentially repeated with respect to the axis of rotation. For example, the compartments of the solid support shown in FIG. 6 are symmetric with respect to the axis of rotation. This means that when the solid support 600 is rotated in a slow pace at non horizontal orientation, all defined areas will have essentially the same liquid drain pattern when reaching the most elevated position. In contrast, the compartments of the solid support shown in FIG. 1 are not symmetric with respect to the axis of rotation. Hence, when rotating the solid support 100 clockwise in a tilted orientation, defined area 119 would reach the most elevated position before defined area 120, and the liquid in the compartment would have more time to drain from defined area 119 than from 120, because 119 is located upstreams. To achieve a reasonably similar liquid drain from these two defined areas, which is required for using one defined area as reference, the rotation must be conducted at slow pace, approximately 0.1-3 rotations per minute. In the case of a rectangular solid support such as the one illustrated in FIG. 3 or FIG. 5, the arms appear in a repeated manner with respect to the axis of rotation. Under the assumption that the axis of rotation is horizontal, approximately the same amount of liquid would enter each arm upon tilting the rectangular solid support from a position where the connection point is in the lower end. Any deviation from horizontal of the rotational axis would result in more liquid entering the lower located arm than the adjacent upper located arm(s), which could in turn result in unevenly distributed drain of liquid in the connected arms resulting in different temporary reduction of liquid during detection.

The technical difficulty of uneven temporary reduction of liquid that can appear when using a circular solid support with multiple compartments, for example as the one illustrated in FIG. 1, can be overcome. If solid support 100 is placed on an inclined, slowly rotating support holder, and liquid is placed in one of the compartments, the first of the two defined areas that approach the most elevated part will have less liquid remaining on it than the second defined area. This is because during the first half of the upward rotation, liquid will cross the low divider, but become captured on the high divider, effectively keeping the liquid on the second defined area for longer time than on the first. The result is that the subtraction of the signal from the reference area might be systematically erroneous. One potential method to overcome this problem is to rotate the solid support approximately one rotation between each measurement. For example, it would be possible to quickly rotate ¾ or ⅞ rounds, then wait a few seconds for the liquid to drain from the most elevated position, and finally conduct a measurement. It would alternatively be possible to rotate ⅝ or ⅞ rounds between every measurement. In general, to reduce the uneven drain of liquid it is essential to rotate the dish more than 90 degrees (preferably more than 120 degrees, and even more preferably more than 180 degrees) before conducting a measurement, because the defined area becoming elevated after such a rotation will have been placed near to lower position a short time prior to the detection. From a general perspective, when a solid support has in total N defined areas (distributed over M different compartments and at least two defined areas per compartment, i.e. $M*2 \leq N$), it is beneficial to rotate at least $(N/2+1)/N*360$ degrees. It will often be suitable to rotate $(N-1)/N*360$ degrees or $(N+1)/N*360$ degrees.

Hence, the seemingly simple development from the single liquid solid support described in prior art (WO2005080967) to a solid support that has more than one compartment, each compartment having at least two defined areas, and where the compartments are non-symmetrical with respect to the axis of rotation, introduces a difficult problem in the above-described uneven liquid draining pattern that require innovation to be overcome. The uneven liquid drain is a deceiving problem, because under ideal conditions the effect of uneven drain is small. Ideal conditions constitutes the combination of a large amount of target (species of interest) attached to one of the defined areas in a compartments, strong interaction between the species in solution and the target, highly purified species in solution so that a neglectable amount of detectable label is present in the liquid, and finally low concentration of the species in solution. Under such circumstances, molecular interaction theory indicates that a large proportion of the labeled species in solution is indeed bound to the target, meaning that the signal from unbound species in solution present in the thin liquid layer remaining after temporary reduction of liquid will be small in comparison to the signal from bound species. In this situation, unbalanced liquid drain has small to moderate impact on the end results. However, as soon as non-ideal conditions occur, liquid drain becomes an error source to consider.

One potential non-ideal condition is low binding strength (also known as low affinity) between species in solution and target. At low affinity, a higher concentration of species in liquid must be present for the interaction to occur and the fraction of bound species is small. Under low-affinity conditions, the signal from unbound species in solution present in the thin liquid layer remaining after temporary reduction of liquid will be similar to or even larger than the signal from bound species, and here an uneven drain may affect or even destroy the possibilities of measuring the interaction.

Another potential non-ideal condition is when the labeling of the species in solution includes a poor purification step or even omitted purification step. In some cases, the availability of species in solution is limited, and small amounts of species are difficult to purify in an efficient manner. In this case, the signal from unbound species in solution present in the thin liquid layer remaining after temporary reduction of liquid may be similar to or even larger than the signal from bound species (depending on the degree of purification), and here an uneven drain may affect or even destroy the possibilities of measuring the interaction.

Still another potential non-ideal condition is when the labeling of the species is conducted in a manner that also irrelevant proteins are labeled at the same time. For example, it is common to store species in a solution containing bovine serum albumin (BSA), where the BSA acts as a protective agent. Then labeling such a solution, both the species and BSA will carry labels. Purification of such a labeled liquid will probably remove unconjugated fluorophore from the sample, but will probably not separate BSA from species (unless the molecular weight of BSA and species differ largely). Under such circumstances, non-ideal conditions for molecular interactions are obtained.

Yet another potential non-ideal condition is when the species is partly denatured, i.e. species consist of one fraction of functional protein and one fraction of denatured protein. In such a situation, the concentration of active species is lower than the total concentration of species, as discussed in "Active concentration measurements of recombinant biomolecules using biosensor technology." by Zeder-Lutz G and co-authors as published in J Mol Recognit. 1999 September-October; 12(5):300-9. Which is incorporated by reference herein. The practical effect on the interaction measurement is identical to the one discussed above related to irrelevant proteins, where the denatured fraction of protein in this case corresponds to the irrelevant protein in the previous case.

Some of the non-ideal conditions are impossible to determine upfront. This means that in a measurement situation, a method that does not adequately handle the uneven liquid drain may miss true interactions due to non-ideal conditions. This is particularly true for weak, low affinity interactions.

EXAMPLE 1

To exemplify the function of the principle of this invention, a circular solid support was manufactured by using a regular untreated polystyrene Petri dish (87 mm diameter, approximately 15 mm height), and adding dividers made of epoxy glue. The manufactured dish 1100 had one first (high) divider 1101 of approximately equal height as the Petri dish, said high divider dividing the Petri dish into two independent compartments (one of them indicated as a striped area 1104). There was one low divider 1102 per compartment and a center elevation 1103 both extending approximately 2 mm from the dish bottom. There were four defined areas (1111, 1112, 1113 and 1114) in the dish. When placed in horizontal position, a liquid containing mouse monoclonal antibody (mmAb) was added to two of the defined areas (1111 and 1113) so as to coat the surface with mmAb. At the same time, the other two defined areas (1112 and 1114) were contacted with a liquid containing bovine serum albumin (BSA) so as to coat these defined areas with BSA, where BSA was intended to be the reference area. After 12 hours, the compartments were washed with a blocking buffer to coat any remaining surface (e.g. the center elevation and the interior sides of the high divider) followed by a wash to remove any non-adsorbed mmAb. This means that in this example, mmAb is the first species or the target. Next, the solid support was placed in the sloping and rotating cell dish holder in LigandTracer Green. One mL of phosphate buffer supplemented with 0.1% BSA was added to each of the two compartments. When oriented so that the high divider was horizontal, the liquid in the lower compartment reached approximately 10 mm above the bottom in the lowest position as indicated by the surface of the liquid pool as a dashed line 1120, high above the height of the low divider 1102. For the higher compartment the liquid was extending a few millimeters above the bottom on the high divider 1101 as indicated by the surface of the liquid pool as a dashed line 1121. This made it possible for the liquid in the respective compartments to stay homogenous throughout the assay, because once every rotation any compartment will be located at the lowest position. In this tilted and rotating orientation, the detector of the instrument was set to register the amount of fluorescent dye in a manner that produced one complete measurement of all defined areas in approximately 45 second. The dish was rotated one quarter (90 degrees) between each measurement. To begin with, the instrument was allowed to collect baseline data during approximately 20 minutes with only buffer present in the compartments. After the baseline reading a fluorescently labeled goat-anti-mouse antibody (fgmAb) was added to the compartments 1131: in one compartment (the one with defined areas 1113 and 1114) fgmAb was added to provide a final concentration of 10 nM and in the other compartment fgmAb was added to provide a final concentration of 1 nM. This means that fgmAb is the second species or the ligand in this example.

The formation of the interaction of the fgmAb and the mmAb was followed during approximately 6 hours. Then (1132) the instrument was stopped, the liquid was aspirated from the compartments, and 1 mL buffer devoid of fgmAb was added to each compartment. The instrument was then restarted and let run over night. The resulting binding curves correspond to signal from active (mmAb) defined area minus the corresponding reference area. Curve 1141 is therefore signal from 1113 minus signal from 1114 and curve 1142 corresponds to signal from 1111 minus signal from 1112. The binding of fgmAb at higher concentration (10 nM) gave a higher signal 1141 than what the binding of the fgmAb at a lower (1 nM) concentration 1142.

This example illustrates that it is possible to produce a solid support which has two different compartments and make a real biochemical measurement using it. Each compartment had a low divider and a center elevation to make it possible to divide the defined areas during the coating procedure, but the divider was low enough to allow added liquid to cross the low divider when placed on the inclined dish holder in the LigandTracer instrument. This example was conducted using close to ideal conditions.

EXAMPLE 2

This example was conducted using the same experimental conditions as example 1. The difference between example 1 and example 2 is the order of, timing of, and quantity of fgmAb. Example 2 was conducted using close to ideal conditions. The two compartments are denoted A and B in this example. FIG. 12 displays the obtained signal, presented for each compartment as signal from the defined reference area subtracted from the signal from defined area holding target (species of interest, mmAb in this case). Signal from compartment A is displayed as a solid curve and signal from compartment B is displayed as a dashed curve.

In compartment A, 6.7 nM fgmAb was added at t=0.75 h and this resulted in a clear binding signal 1201. The solution was replaced with pure buffer at t=3 h which resulted in a steady signal 1202. 6.7 nM fgmAb was once added again at t=5.5 h which resulted in an increasing signal 1203.

The association of 6.7 nM fgmAb was followed in compartment B between t=1.75 h and t=4.25 h 1211. The dissociation (Concentration=0 nM) was measured between t=4.25 and 5.5 h 1212. At 5.5 h, 20 nM fgmAb was added to compartment B resulting in rapidly increasing signal 1213.

No signal increase was observed in compartments where no fgmAb was present, i.e. there were no signs of cross-over of the antibody solution between the two compartments. This example hence shows that under close to ideal conditions it is possible to measure interactions in two different compartments in an independent manner, i.e. having different liquids and their own defined areas.

EXAMPLE 3

This example was conducted using the same experimental conditions as example 1 except for the following changes. Rotation of the solid support during measurement was changed regularly during the measurement. The dish was either rotated one quarter (90 degrees) between each measurement, or three quarters ((4−1)/4*360 degrees=270 degrees). The two compartments are denoted A and B in this example. In compartment A the measurement was conducted using close to ideal conditions. In compartment B, the measurement was conducted using non-ideal conditions, obtained by supplementing the liquid with an irrelevant protein labeled with a fluorophore so as to elevate the total amount of fluorescence in the liquid. This addition of fluorophore presents an identical problem as (a) poor purification of the species in solution after labeling and (b) support protein present during labeling.

FIG. 13 displays the obtained signal, presented for each compartment as signal from the defined reference area subtracted from the signal from defined area holding target (species of interest, mmAb in this case). Signal from compartment A is displayed as a solid curve 1310 and signal from compartment B is displayed as a dashed curve 1320. The periods of time where the dish was rotated one quarter (90 degrees) are indicated with horizontal lines 1301. At approximately 40 minutes, 6 nM of fgmAb was added to each of the two compartments. In compartment A with close to ideal conditions, binding was detected the same irrespective of how the dish was rotated. In compartment B, with non-ideal conditions, the binding curve 1310 is deviating from the curve obtained under ideal conditions 1320 during times when one quarter rotation was implemented. The amount of added irrelevant protein was approximately the same as the amount of added fgmAb, indicating that only a small amount of additional irrelevant protein is required to induce non-ideal conditions and the corresponding problems during detection with non-symmetrical compartments.

This example shows that when measuring molecular interaction in a multi-compartment dish, non-ideal conditions that commonly occur may negatively impact the quality of results or may even destroy the capability to measure molecular interactions.

EXAMPLE 4

This example describes one possible application of the present invention as applied to cell-based interaction analysis. Cells of type SKOV-3 known to express the HER2 receptor is grown on defined areas 1111 and 1113 of a solid support of type 1100. Defined areas 1112 and 1114 are left empty for reference purposes. After cells has attached firmly to the solid support, it is placed in a LigandTracer Grey device. Approximately 1 mL of RPMI cell culture medium is added to each compartment.

After an initial baseline measurement, the antibody trastuzumab, labeled with iodine 125 and purified after labeling, is added at the concentration 1 nM to one compartment and at the concentration 4 nM to the other compartment. The binding of labeled trastuzumab is followed in a time-resolved manner, independently from the two compartments holding different concentration of trastuzumab. The output shows that the compartment having higher concentration of trastuzumab will have a steeper upward slope in the initial phase of the binding process.

When repeating this measurement, trastuzumab is labeled with iodine 125 but the labeled aliquot is not purified. The measurement is repeated using a solid support prepared with SKOV-3 cells as described above and with 1 and 4 nM antibody addition to the respective compartments. If the measurement is conducted with three quarters ((4−1)/4*360 degrees=270 degrees) rotations between each detection event, results are more similar to the measurement results from the purified antibody than if the measurement is conducted using only one quarter (90 degrees) rotation between each detection event.

Details regarding how to conduct cell culturing and antibody labeling protocols are available in the publication "Protein interactions with HER-family receptors can have different characteristics depending on the hosting cell line" by Barta and co-authors as published in INTERNATIONAL JOURNAL OF ONCOLOGY 40: 1677-1682, 2012, which is incorporated by reference herein.

EXAMPLE 5

This example was conducted using the same experimental conditions as example 1 except for the following changes. A431 cells, known to express epidermal growth receptor, were cultured to form an adhered layer of cells in defined areas 1111 and 1113. Reference areas 1112 and 1114 had no cells attached. The low dividers were in this example hydrophobic barriers, created by use of a pen with hydrophobic liquid. Approximately one mL of cell culture RPMI medium was added to each compartment. Fluorescently labeled cetuximab, known to bind to the epidermal growth receptor, was used as ligand (species in solution). Rotation of the solid support during measurement was changed regularly during the measurement. The dish was either rotated one quarter (90 degrees) between each measurement, or three quarters ((4−1)/4*360 degrees=270 degrees). The two compartments are denoted A and B in this example. In compartment A the measurement was conducted using close to ideal conditions. In compartment B, the measurement was conducted using non-ideal conditions, obtained by supplementing the liquid with an irrelevant protein labeled with a fluorophore so as to elevate the total amount of fluorescence in the liquid. This addition of fluorophore presents an identical problem as (a) poor purification of the species in solution after labeling and (b) support protein present during labeling.

FIG. 14 displays the obtained signal, presented for each compartment as signal from the defined reference area subtracted from the signal from defined area holding target (species of interest, A431 cells in this case). Signal from compartment A is displayed as a solid curve 1410 and signal from compartment B is displayed as a dashed curve 1420. The periods of time where the dish was rotated one quarter (90 degrees) are indicated with horizontal lines 1401. Baseline measurement was conducted between 80 minutes and 120 minutes, i.e. before adding fluorescently labeled cetuximab. At approximately 130 minutes, 6 nM of fluorescently labeled cetuximab was added to each of the two compartments. In compartment A with close to ideal conditions, baseline was not disturbed by changes in rotation method, but in compartment B a clear difference is visible when comparing baseline measured at one quarter rotation and three quarter rotation. During binding, compartment A and B produce similar results for three quarter rotation. During one quarter rotation, both the ideal and the non-ideal conditions deviated from the results using three quarter rotation.

This example shows that when measuring molecular interaction on cells in a multi-compartment dish, both ideal and non-ideal conditions that commonly occur may negatively impact the quality of results or may even destroy the capability to measure molecular interactions.

The invention claimed is:

1. A measurement device for measurement of an interaction of two different species, the measurement device comprising:
 a circular solid support, formed of a bottom surface and a wall extending upward from an outermost circumferential edge of the bottom surface and delimiting an interior of the circular solid support, the circular solid support including, within said interior, first dividers that form the interior of the circular solid support into at least two independent compartments; and
 a rotator configured to rotate the circular solid support at an inclined orientation,
 the circular solid support having a circular geometry such that each compartment of said compartments is shaped as a circular segment,
 a center of the circular solid support having an elevated part extending upward with respect to the bottom surface, the first dividers each extending from said elevated part at the center to a periphery of the circular solid support at an inner-facing surface of the wall, said circular solid support arranged to, during use, rotate about a rotational axis at said center and tilt into the inclined orientation in which said bottom surface is in a non-horizontal orientation,
 said compartments being distributed in a regular manner with respect to the rotational axis, and each compartment of said compartments having identical geometry and being non-symmetric seen alone from perspective of the rotational axis,
 an interior of each compartment of said compartments being configured so as to contain liquid, and each compartment comprising at least two non-overlapping defined areas with at least one of said non-overlapping defined areas being designated as a reference area,
 said compartments being separated from each other by said first dividers which provide a barrier to fluid flow from one compartment to another during use, the liquid containing a second species, so as to cover the defined portion of the circular solid support,
 temporarily reduce an amount of said liquid in contact with the defined portion holding said first species, said reduction carried out so the amount of liquid that remains on the defined area is less than 10% of the amount of liquid present in vicinity of the defined area when the circular solid support is positioned horizontally in rest, and
 perform a measurement of the defined portion covered with a temporarily reduced amount of liquid such that said measurement detects an interaction between said first species and said second species,
 said temporarily reduced amount of liquid comprising a reduction of the amount of liquid near at least one of said defined areas without changing a total amount of liquid in contact with any of said compartments in said circular solid support,
 said temporarily reduced amount of liquid accomplished by rotating the circular solid support with said circular solid support in the non-horizontal orientation such that a portion of the circular solid support at any time is immersed in said liquid,
 wherein the measurement device rotates the circular solid support more than 90 degrees before the measurement is performed, and
 wherein the measurement device is configured to wait a few seconds for liquid to drain from a most elevated position of the circular solid support in the non-horizontal orientation before the measurement is performed.

2. The measurement device as claimed in claim 1, wherein for M number of compartments of said circular solid support, and for N number of defined areas of said circular solid support, each compartment of said compartments containing at least two defined areas, the circular solid support is rotated by the measurement device by one of (N/2+1)/N*360 degrees, (N−1)/N*360 degrees, or (N+1)/N*360 degrees between each measurement.

3. The measurement device as claimed in claim 1, wherein the circular solid support is rotated by the measurement device by ¾ of one rotation between each measurement.

4. The measurement device as claimed in claim 1, wherein the circular solid support is rotated by the measurement device by ⅞ of one rotation between each measurement.

5. The measurement device as claimed in claim 1, wherein an exterior side of the wall of said circular solid support includes non-evenly spaced grooves adapted to mate with corresponding pins on a holder of the rotator, whereby said device is attachable to said holder in a single orientation.

6. The measurement device as claimed in claim 1, wherein at least one of said first and second dividers are made of solid material.

7. The measurement device as claimed in claim 1, wherein said second dividers are provided as hydrophobic areas between the defined areas.

8. The measurement device as claimed in claim 1, wherein at least one of said first and second dividers comprise a material that shields an emission of a fluorescent or radioactive label.

9. The measurement device as claimed in claim 1, wherein at least one of said first and second dividers comprise a slit for housing a shielding material.

\* \* \* \* \*